United States Patent [19]

Mueller et al.

[11] Patent Number: 5,181,920
[45] Date of Patent: Jan. 26, 1993

[54] ATHERECTOMY DEVICE WITH ANGIOPLASTY BALLOON AND METHOD

[75] Inventors: Richard L. Mueller, Mountain View; Brian E. Farley, Los Altos; James F. Pfeiffer, Cupertino, all of Calif.

[73] Assignee: Devices for Vascular Intervention, Inc., Redwood City, Calif.

[21] Appl. No.: 624,855

[22] Filed: Dec. 10, 1990

Related U.S. Application Data

[63] Continuation-in-part of Ser. No. 536,041, Jun. 8, 1990, abandoned.

[51] Int. Cl.$^5$ .................................................. A61B 17/32
[52] U.S. Cl. ........................................ 606/159; 606/171; 606/180; 604/22; 604/96
[58] Field of Search ............... 604/22, 96; 128/750, 128/751, 752, 753, 754, 755; 606/159, 170, 171, 180

[56] References Cited

U.S. PATENT DOCUMENTS

| | | |
|---|---|---|
| 3,614,953 | 10/1971 | Moss . |
| 4,228,802 | 10/1980 | Trott . |
| 4,273,128 | 6/1981 | Lary . |
| 4,274,414 | 6/1981 | Johnson et al. . |
| 4,292,974 | 10/1981 | Fogarty et al. . |
| 4,445,509 | 5/1984 | Auth ................................ 606/159 |
| 4,627,436 | 12/1986 | Leckrone . |
| 4,631,052 | 12/1986 | Kensey . |
| 4,646,736 | 3/1987 | Auth . |
| 4,653,496 | 3/1987 | Bundy et al. . |
| 4,655,746 | 4/1987 | Daniels et al. . |
| 4,664,112 | 5/1987 | Kensey et al. . |
| 4,669,469 | 6/1987 | Gifford, III et al. ........... 606/159 |
| 4,685,458 | 8/1987 | Leckrone . |
| 4,696,667 | 9/1987 | Masch . |
| 4,728,319 | 3/1988 | Masch . |
| 4,729,763 | 3/1988 | Henrie . |
| 4,732,154 | 3/1988 | Shiber . |
| 4,749,376 | 6/1988 | Kensey et al. . |
| 4,754,755 | 7/1988 | Husted . |
| 4,772,258 | 9/1988 | Marangoni et al. . |
| 4,784,636 | 11/1988 | Rydell ................................ 604/22 |
| 4,892,519 | 1/1990 | Songer et al. ..................... 606/159 |
| 4,926,858 | 5/1990 | Gifford, III et al. .............. 606/159 |

FOREIGN PATENT DOCUMENTS 0163502 5/1985 European Pat. Off. .

Primary Examiner—John D. Yasko
Assistant Examiner—William Lewis
Attorney, Agent, or Firm—Townsend and Townsend

[57] ABSTRACT

An atherectomy device for reducing stenosis material from a vascular vessel is provided. The atherectomy device includes an elongated flexible tubular member having at least one lumen extending therethrough and having proximal and distal extremities. A flexible drive means disposed within the tubular members is free to move both rotationally and axially therein. A cutting assembly is carried by the distal extremity of the flexible tubular member with a cutter being carried by the distal extremity of the flexible drive means for removing a portion of the stenosis from the vessel wall. An inflatable dilation balloon is carried by the tubular member proximally of the cutter for further reducing the stenosis after initial reduction by the cutter. A perfusion channel maintains blood flow past the dilation balloon. Methods of the present invention include cutting and dilating a stenosis, cutting then immediately dilating a stenosis, and dilating then immediately cutting a stenosis.

19 Claims, 3 Drawing Sheets

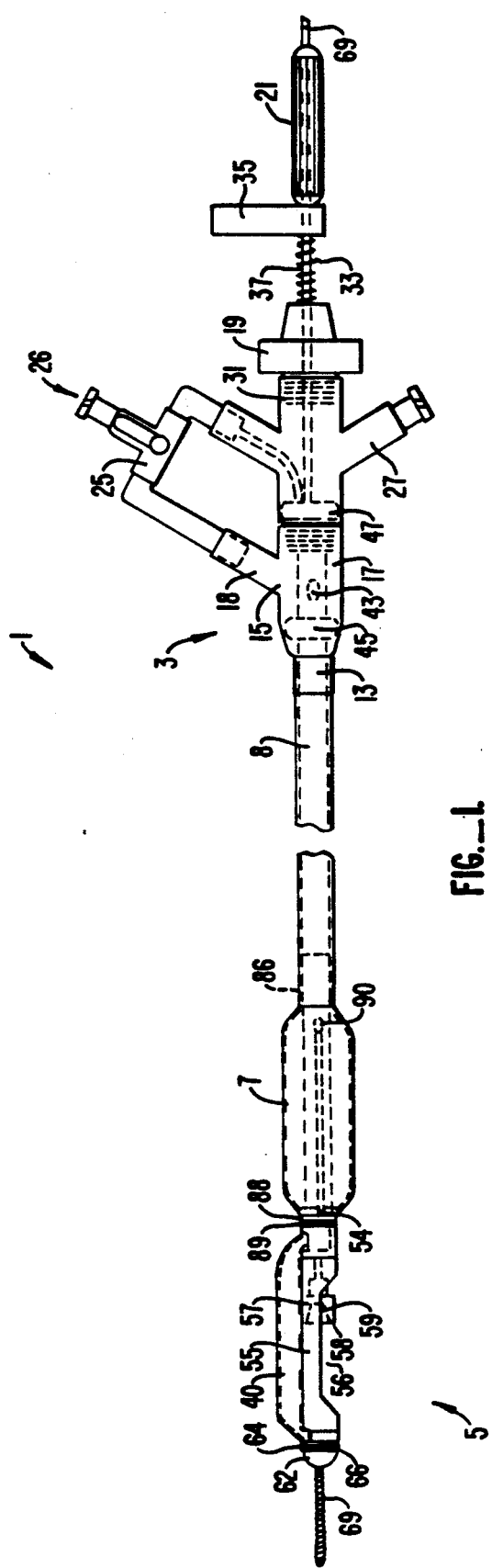
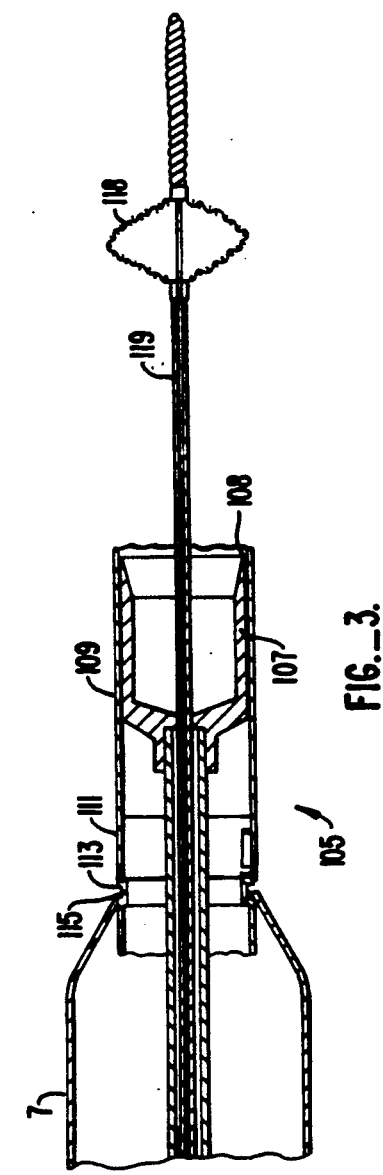
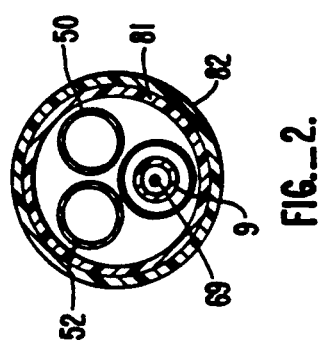

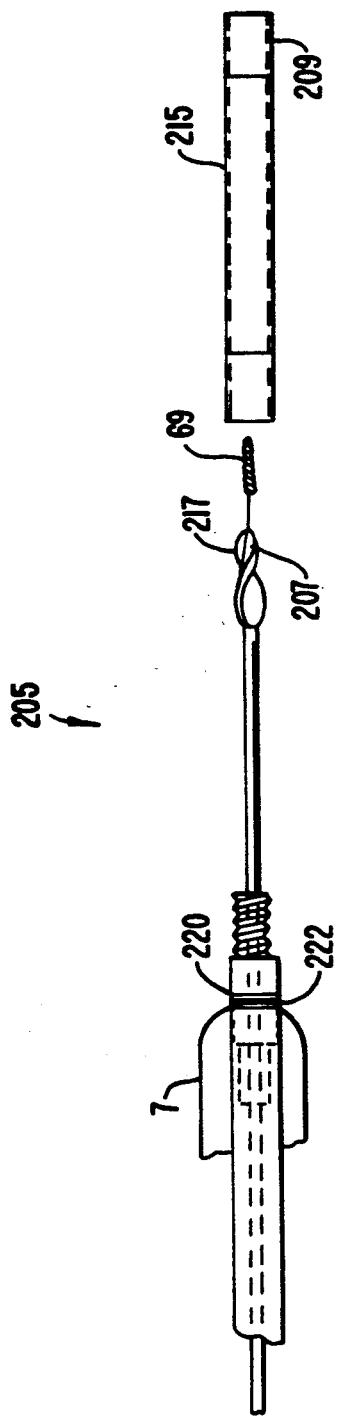
FIG._4.
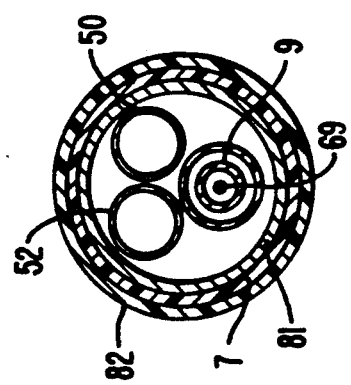
FIG._5.

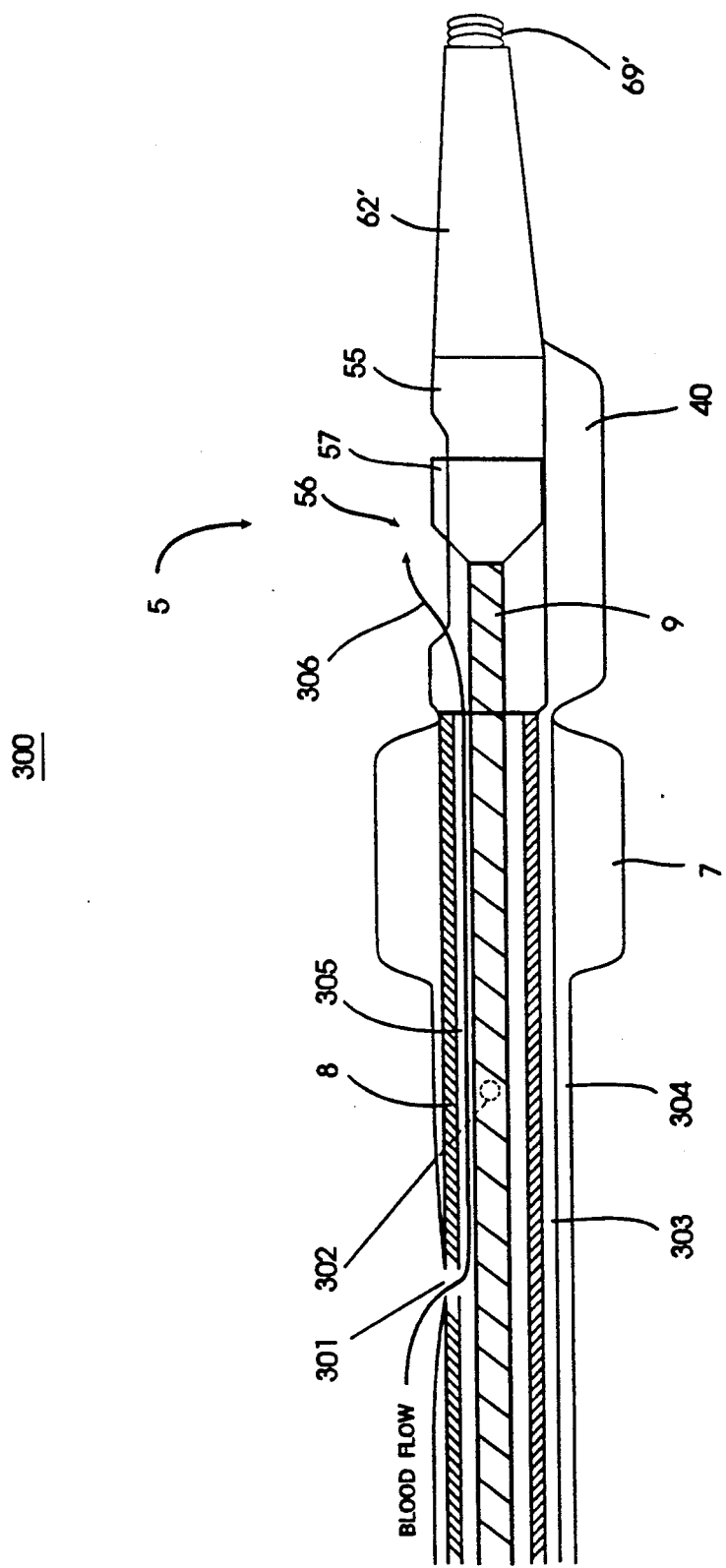
FIG._6

5,181,920

ATHERECTOMY DEVICE WITH ANGIOPLASTY BALLOON AND METHOD

The present invention is a continuation in part of application Ser. No. 07/536,041 filed on Jun. 8, 1990, now abandoned, the disclosure of which is incorporated herein by reference.

BACKGROUND OF THE INVENTION

The present invention relates generally to an atherectomy device and method for reducing stenosis within vascular vessels.

Coronary and peripheral vascular arteriosclerosis, known also as atherosclerosis, is a common ailment occurring in humans which involves deposition of fatty-like substances called atheroma or plaque on the walls of blood vessels. These plaque deposits are most common in the peripheral blood vessels that feed the limbs of the human body and the coronary arteries which feed the heart. When long term plaque build-up reaches the point of nearly totally occluding a vessel, a thrombus (clot) type attachment can occur resulting in a long segment of soft vessel occlusion. Occasionally these fatty deposits occur in fairly localized regions of a blood vessel, thereby restricting the blood's flow and imposing a serious risk to the person's health.

In the past, several methods have been attempted to restore normal blood flow through the affected vessels. Traditionally, major surgery was the only practical means for treating occlusions. More recently, there has been substantial success in increasing the size of the flow passage within occluded vessels through the use of a dilation process known as balloon angioplasty. However, in a substantial percentage of the cases where balloon angioplasty is used, the removed plaque deposits will reoccur.

More recently, there has been an interest in atherectomy devices that actually cut through stenosis within a vessel regardless of whether the stenosis is primarily a plaque type deposit or a thrombus type clot. For example, U.S. Pat. No. 4,669,469 discloses a side cutting atherectomy device for removing material from an atheroma in the vascular system. Similarly, co-pending applications Ser. Nos. 045,916 filed May 1, 1987 and 117,072 filed Nov. 5, 1987, which are incorporated herein by reference, disclose alternative designs for end cutting atherectomy devices.

A drawback of such atherectomy devices is that they may leave rough edges when cutting. Additionally, since the cutter size is restricted, it is not always possible to open a passage as large as desired when using such devices. Further, such devices are not capable of securely anchoring the atherectomy device in place while cutting proceeds.

Another disadvantage of present devices is their inability to treat some occlusive complications, particularly those which arise during the periatherectomy period and require immediate attention. For example, diffuse or long atherosclerotic lesions are susceptible to abrupt closure (vessel occlusion) after angioplasty or atherectomy. This potentially fatal complication is best treated by successive dilation of the stenosis to re-establish perfusion to the heart muscle. To be successful, a balloon must be rapidly passed across the stenosis for redilation.

Thus, in some cases, it may be desirable or necessary to follow atherectomy with angioplasty. The use of a separate angioplasty balloon, however, results in significant delays in treatment. For example, time is lost in removing the atherectomy device, preparing the balloon for introduction, and accessing the lesion before performing the dilations. The removal of the atherectomy device may even cause the physician to lose access to the lesion altogether, thus preventing the later introduction of a balloon catheter. Since longer periods of vessel occlusion lead to increased heart muscle damage and worsening of eventual patient outcome, the desirability for immediate treatment is apparent.

What is needed is an atherectomy device with the added capability of promptly treating attendant complications, such as abrupt closure. The present invention fulfills this and other needs.

SUMMARY OF THE INVENTION

Therefore, it is a primary objective of the present invention to provide an atherectomy device that is particularly well suited for reducing stenosis materials that occlude a blood vessel.

Another objective of the invention is to provide an atherectomy device with an inflatable member that may be used to smooth the sides of an expanded passage cut through a stenosis Within a vessel.

Another object of the invention is to provide an atherectomy device capable of dilating a vessel to further reduce a stenosis after some cutting has occurred.

Another objective of the invention is to provide a means for setting an atherectomy device while cutting occurs.

Another objective of the invention is to provide an atherectomy device capable of concurrently cutting and dilating a vessel to reduce complications and restenosis rate while achieving larger lumenal areas.

Another objective of the invention is to provide an atherectomy device capable of promptly treating occlusive complications.

To achieve the foregoing and other objects and in accordance with the purpose of the present invention, an atherectomy catheter for removing at least a portion of a stenosis within a vessel is provided having a cutting assembly and an inflatable member. The atherectomy catheter includes an elongated flexible tubular member having at least one lumen extending therethrough. In an alternative embodiment, the tubular member includes perfusion means for maintaining blood flow. A flexible drive means is disposed within the tubular member and is mounted for axial and rotational movement therein. A cutter is carried by the distal extremity of the flexible drive means. The inflatable member, which may take the form of a dilation balloon, is carried by the tubular member proximally of the cutter with the interior of the inflatable member being in communication with a lumen in the flexible tubular member.

The atherectomy catheter also preferably includes flexible guiding means extending forward of the cutter for guiding the cutter to travel axially within the vessel and collection means for collecting the removed stenosis materials. Additionally, inflation means is provided for inflating and deflating the inflatable member. Preferably the cutter and flexible drive means are movable axially relative to the tubular member.

The methods of the present invention include atherectomy (cutting) performed concurrently with angioplasty (dilation). Different dilation balloon pressures may be used. For example, in one method initial cuts can be made at low balloon inflation pressures. The pressure is increased so that by the end of the procedure, the dilatory effect predominates. In another method, initial cuts are made at high balloon inflation pressures. The balloon is deflated so that cutting predominates at the end of the method.

Another method includes atherectomy immediately followed by angioplasty. Cuts are made without dilation. Then, the dilation balloon is positioned proximate the stenosis and inflated. The technique is particularly useful for averting occlusive complications.

In yet another method of the present invention, angioplasty is immediately followed by atherectomy. Cuts may be made before the vessel recoils from dilation.

The features of the present invention that are believed to be novel are set forth with particularity in the appended claims. The invention, together with further objects and advantages thereof, may best be understood by reference to the following description of the presently preferred embodiment, taken in conjunction with the accompanying drawings.

BRIEF DESCRIPTION OF THE DRAWINGS

FIG. 1 is a diagrammatic side elevational view of a catheter constructed in accordance with the present invention.

FIG. 2 is a cross-sectional view taken along line 2—2 of FIG. 1 highlighting a possible construction for an elongated tubular member suitable for use with the device shown in FIG. 1.

FIG. 3 is a diagrammatic side view of an alternative cutting assembly incorporating the present invention.

FIG. 4 is a diagrammatic side view of another cutting assembly that incorporates the present invention.

FIG. 5 is a cross-sectional view taken along line 5—5 of FIG. 1 which highlights a tubular member construction suitable for securing the angioplasty balloon.

FIG. 6 is a diagrammatic side view of an alternative embodiment constructed in accordance with the principles of the present invention, wherein the tubular member includes a means for maintaining arterial perfusion.

DETAILED DESCRIPTION OF THE PREFERRED EMBODIMENT

As shown in the drawings, an illustrative embodiment of the atherectomy catheter 1 of the present invention includes a proximal actuator assembly 3, a cutter assembly 5, an inflatable member 7 and a tubular member 8 that connects proximal actuator assembly 3 to cutter assembly 5. A flexible drive means 9 is disposed within tubular member 8 and is adapted for rotational and axial movement therein. The cutter assembly 5 is carried by the distal extremity of tubular member 8. The inflatable member 7 may take the form of a dilation balloon and is carried by tubular member 8 proximally of cutter assembly 5.

In one embodiment of the present invention, as shown in FIG. 1, the cutter assembly 5 is constructed substantially identically with cutter assembly described in co-pending application Ser. No. 732,691 filed May 10, 1985. Specifically, a housing 55 protects a cutter 57 carried therein and is mounted on the distal extremity of the flexible tubular member 8 and an inflatable member in the form of atherectomy balloon 40 is provided to position the housing 55 and cutter 57 relative to a stenosis disposed on one side of the atherectomy catheter 1.

The proximal actuator assembly 3 includes a coupling member 13, an angioplasty port 15, a three arm adapter 17 threadably connected to a thumb screw 19 and a drive shaft 21. Coupling member 13 is secured to tubular member 8 by any suitable means such as gluing. Angioplasty port 15 is threadably secure between coupling member 13 and three arm adapter 17, and has an arm 18 attached to valve 25. Three arm adapter 17 itself includes a flush port 27 and an atherectomy port 28. Atherectomy port 28 is also attached to the valve 25. The valve 25 includes a fluid access port 26 for receiving fluids and a switch mechanism for directing the fluid flow to either angioplasty port 15 or atherectomy port 28. Access port 26 is connected to a fluid source (not shown) which provide saline solution that may be used to inflate the inflatable members 7 and 40. Since it is contemplated that only one of the two inflatable members (dilation balloon 7, atherectomy balloon 40) will be inflated or deflated at a time, the switching mechanism facilitates selective communication between the fluid source and the two inflatable members 7, 40. Thumb screw 19 is threadably coupled to the third arm of three arm adapter 17 while O-ring seal 31 prevents fluid from leaking from the atherectomy catheter 1. Drive means 9 which takes the form of a braided drive cable is anchored in drive tube 33 which forms an extension of drive shaft 21. Drive tube 33 passes coaxially through thumb screw 19 and is firmly adhered to drive shaft 21.

It will be appreciated that the drive cable 9 can be moved rotationally relative to tubular member 8 by rotating drive shaft 21. Additionally, drive cable 9 can be moved axially relative to tubular member 8 by pushing thumb lever 35 toward thumb screw 19 against the pressure of spring 37 which is placed about drive tube 33 between thumb screw 19 and drive shaft 21. When tension is released from thumb lever 35, compression spring 37 will cause thumb lever 35 and thumb screw 25 to separate thereby causing drive cable 9 and hence cutter 57 to move axially relative to housing 55. The cutter 57 works best when rotated at a high rate of speed. Therefore, drive shaft 21 on proximal assembly 3 is preferably spliced and adapted to be coupled to a motorized drive unit (not shown). A suitable motorized drive unit is disclosed in co-pending application Ser. No. 031,168 filed Mar. 26, 1987. A suitable rotational speed for the cutter 57 is approximately 2500 RPM. A guide wire 69 may extend coaxially through a lumen in drive cable 9 and drive shaft 21 and may be free to move longitudinally therethrough to facilitate introduction of the catheter.

Tubular member 8 is formed of a three-lumen core tubing as seen in FIG. 2. The outer portion of tubular member 8 may be formed in any conventional manner. By way of example, the tubular member 8 may be formed of a braided torque transmitting layer 81 encased by a shrink fit jacket 82. The torque transmitting layer 81 carries an angioplasty lumen 50 and an atherectomy lumen 52 in addition to drive cable 9. To inflate dilation balloon 7, valve 25 is actuated such that access port 26 communicates with an arm 18 of angioplasty port 15. The angioplasty lumen 50 includes an input aperture 43 that facilitates fluid communication between angioplasty port 15 and the interior of angioplasty lumen 50. Leak proof seal 45 seals the connection between angioplasty port 15 and coupling member 13 while seal 47 prevents fluid from leaking between angioplasty port 15 and the three arm adapter 17.

When the atherectomy balloon 40 is to be inflated or deflated, valve 25 is switched such that access port 26 is in fluid communication with atherectomy lumen 52.

In the embodiment shown in FIG. 1, the cutter assembly includes a housing 55 mounted at the distal extremity of the flexible tubular member 8 and can be formed of suitable materials such as stainless steel. It is generally cylindrical as shown and has its proximal extremity secured to housing tail piece 54 as shown in FIG. 2. A cutout 56 is provided in the housing 55 in one side thereof and faces in a direction which is generally perpendicular to the longitudinal axis of the housing 55. A work performing device in the form of a cutter 57 is slidably mounted within the housing 55 and is provided with a circular cutting edge 58 which lies in the plane perpendicular to the longitudinal axis of the housing in the axis of longitudinal movement of the cutter 57. A bell-shaped recess 59 provided within the cutter 57 and extends rearwardly from the cutting edge 58.

Atherectomy balloon 40 is attached to atherectomy lumen 52 by any conventional means such as an adhesive. Atherectomy balloon 40 passes through an aperture 60 in housing tail piece 54. The proximal extremity of the atherectomy balloon 49 is connected in a suitable manner with the atherectomy lumen 52 in the flexible tubular member 8 so that the balloon can be inflated and deflated as desired. The distal extremity balloon of 40 is tied to nose cone 62 in a conventional manner. By way of example, a suitable tie-off technique is to wrap a suitable means such as nylon wire 64 into a recess 66 provided in the nose piece 62. The nose cone 62 is secured to the open distal end of housing 55 by suitable means such as an adhesive. The nose cone 62 is provided with a rounded forwardly extending surface 67.

A conventional flexible elongated guide wire 69 provided with a helical coil spring at its distal extremity is removably mounted in the atherectomy device. The guide wire 69 extends through the hollow flexible drive cable 9, through a bore in cutter 57, the housing 55 and through a bore provided in nose cone 62. The guide wire 69 serves as a guiding element for inserting the catheter into a vessel in the vascular system of a patient.

The inflatable dilation balloon 7 is attached to tubular member 8 directly behind cutter assembly 5. Preferably the dilation balloon 7 is mounted coaxially with tubular member 8 and conventional P.E.T., P.V.C., or polyolefin family dilation balloons may be used.

To secure dilation balloon 7 in place, shrink fit jacket 82 will terminate before the junction with housing tail piece 54 and will be used to hold the proximal end 86 of dilation balloon 7 as shown in FIG. 5. Specifically, the proximal extremity of dilation balloon 7 is glued to torque transmitting layer 81 and heat-shrinkable tubing is adhered in place over the proximal extremity and heat treated to shrink wrap the proximal end 86 of dilation balloon 7, thereby firmly securing it into place. The distal extremity of dilation balloon 7 may be adhered to housing tail piece 54. Additionally, a nylon wire 88 may be wrapped into a recess 89 in housing tail piece 54, thereby firmly securing the dilation balloon 7 to the atherectomy catheter.

Fluid communication between the fluid source (not shown) and dilation balloon 7 is accomplished through valve 25, angioplasty port 15 and angioplasty lumen 50. An aperture 90 in tubular member 8 allows fluid to communicate directly between the interior of dilation balloon 7 and angioplasty lumen 50. The proximal extremity of angioplasty lumen 50 may be blocked to prevent leakage into the interior of tubular member 8. The plugs may be formed of an extruded bead or a suitable adhesive.

An alternative embodiment of the present invention is shown in FIG. 3. In this embodiment a cutting assembly as described in co-pending application Ser. No. 045,916 filed May 1, 1987 is fitted with a dilation balloon in accordance with the present invention. The cutting assembly 105 includes a cutter 107 having a forwardly extending angular cutting surface 108. An expandable basket 118 carried by guide wire 119 may be opened to limit the travel of cutter 107 and retain any severed stenosis material within the cutter. The cutter 107 is recessed within a housing 109 which includes a housing tail piece 111. Housing tail piece 111 includes a recess 113 into which a nylon wire 115 of dilation balloon 7 may be wrapped. In all other respects, the attachment of the dilation balloon 7 is identical to the attachment described with respect to the embodiment shown in FIG. 1. It will be appreciated, however, that the tubular member 8 will have a single angioplasty lumen passing therethrough together with drive cable 9.

FIG. 4 shows yet another embodiment of the present invention in which a dilation balloon 7 is combined with a drill type atherectomy device as disclosed in co-pending application Ser. No. 117,072, filed Nov. 5, 1987. In this embodiment the cutting assembly 205 includes a collection chamber 215 and a housing 209 formed to receive a cutter bit 207. The collection chamber 215 is located proximally of the housing 209 and bit for collecting the removed stenosis material within the atherectomy device. The cutting tool 207 is carried by the distal extremity of flexible drive cable 9. The cutting bit serves to remove materials from the stenosis and cause the removed materials to be withdrawn into the collection chamber through a plurality of helical flutes 217. Guide wire 69 fastens coaxially through the atherectomy catheter. The mounting of the dilation balloon 7 of this embodiment of the atherectomy catheter is identical to the mounting system described for the preceding two embodiments.

FIG. 6 shows yet another embodiment constructed in accordance with the principles of the present invention (only the proximal portion of which is illustrated). Atherectomy device 300 comprises tubular member 8 with drive member 9 disposed therein, cutter assembly 5 attached to the distal end of tubular member 8, and a nosecone 62' having a fixed guidewire 69' coupled to the distal end of cutter assembly 5.

As illustrated, cutter assembly 5 includes housing 55 with cutter 57 disposed therein. Cutter 57 is secured to the forward end of drive means 9. Cutout or aperture 56 is provided along one side of housing 55, thereby allowing cutter 57 to access stenotic material. On an opposing side, housing 55 is coupled to atherectomy balloon 40 which is inflatable through balloon inflation lumen 303.

Tubular member 8 is coupled to dilation balloon 7 which is inflatable through balloon inflation lumen 304. Tubular member 8 further includes a means for maintaining tissue perfusion, i.e., blood flow past the blockage which is created by inflation of dilation balloon 7. Specifically, tubular member 8 is provided with a perfusion hole 301 for receiving arterial blood flow. Perfusion hole 301 communicates directly with an annular lumen 305 defined by the inner wall of tubular member 8 and drive means 9. Tubular means 8 may be provided with additional perfusion holes, for example, perfusion hole 302 located distally and perpendicularly to perfusion hole 301. Lumen 305, in turn, opens distally into cutout 56 of housing 55. Cutout 56 communicates freely with arterial blood (distal to dilation balloon 7). Thus, a perfusion channel 306 is defined wherein blood flows into perfusion hole 301, along lumen 305, and out through cutout 56. Since perfusion channel 306 always remains open (even when dilation balloon 7 is fully inflated), perfusion to the heart muscle is maintained at all times. This permits several new dilation and severing or cutting techniques (discussed hereinbelow).

The aforementioned devices may be used in a wide variety of ways. As alluded to earlier, often after cutting with any of the described cutters, loose end or rough edges will remain which can flap into the open flow channel. Therefore, it is desirable to reduce such loose edges. After the cutting bit has been used to remove a portion of the stenosis to either widen or create a flow path through an artery (or other similar sized vessel), the atherectomy catheter 1 may be advanced so that dilation balloon 7 is disposed directly beside the rough edges. Valve 25 is then switched such that the fluid source (not shown) communicates with dilation balloon 7 to inflate the balloon thereby dilating the vessel and compressing any loose edges into the body of the vessel.

It should be appreciated that a similar technique can be used to further expand a vessel after a flow path the size of a cutter has been opened. (Particularly with cutters such as those shown in FIGS. 3 and 4.) In such a method of operation, an initial cut is made with a cutting device to open a channel through the vessel. The catheter is then advanced so that the dilation balloon underlies an area sought to be expanded. Valve 25 is switched into communication with angioplasty port 15 and fluid is pumped through angioplasty lumen 50 into dilation balloon 7 thereby expanding the balloon and stretching the vessel, as well as compressing the stenosed portion of the vessel walls to create a larger flow path.

Additionally, it will be appreciated, that in some circumstances, it may be desirable to firmly secure the cutting assembly 5 in place when cutting is occurring. In the embodiment shown in FIG. 1, atherectomy balloon 40 is used to position the cutter. It also may serve to secure the cutting assembly in place. However, the embodiment shown in FIGS. 3 and 4 do not have any such attaching mechanism and therefore, if it is desirable to keep the cutting tool in place, dilation balloon 7 can be expanded before cutting proceeds. It will be appreciated that since these cutters operate at the end of an extended flexible tubular member, such anchoring may often be desirable since in some circumstances it is difficult to generate sufficient force to put the cutter through a stenosis (particularly calcified stenoses) absent some form of anchoring.

Additional techniques are available using the embodiment of FIG. 6. Atherectomy device 300 is positioned such that cutter assembly 5 is proximate the stenosis. Atherectomy balloon 40 may be used to anchor cutter assembly 5 in place. Stenotic material is severed by cutter 57. Concurrently, uniform dilation of the vessel is provided by dilation balloon 7 which is separately inflatable through balloon inflation lumen 304. Thus, angioplasty and atherectomy are performed simultaneously.

Since tissue perfusion is maintained by perfusion channel 306, several different dilation techniques may be employed during cutting (atherectomy) without compromise to the heart muscle. As a first variation of the foregoing method, for example, dilation balloon 7 may remain fully inflated during the atherectomy procedure. Thus, maximal dilation may be sustained for as long as necessary.

As a second variation of the foregoing method, dilation balloon 7 is gradually inflated over the course of the procedure. Initial cuts are made at low inflation pressures so that cutting predominates at the beginning of the procedure. Inflation balloon 7 is gradually inflated so that by the end of the procedure, dilation (angioplasty) predominates.

As a third variation, dilation balloon 7 is fully inflated at the outset and then gradually deflated during the procedure. Initial cuts are made at high inflation pressures so that dilation predominates at the beginning of the procedure. By the end of the procedure, dilation balloon 7 has been deflated so that cutting predominates.

Another method of atherectomy device 300 would include performing angioplasty and atherectomy sequentially. First, dilation balloon 7 is positioned proximate the stenosis. Since perfusion is maintained b perfusion channel 306, dilation can be performed by any of the above methods (e.g., sustained, increasing or decreasing inflation). Immediately after dilation, cutter 57 is rearwardly positioned so that it is proximate the angioplasty site and cutting is performed. The technique has the particular advantage of allowing atherectomy immediately after angioplasty—before the vessel wall has had time to recoil.

Another approach is atherectomy immediately followed by angioplasty. First, cutting is performed by cutter 57. Next, dilation balloon 7 is forwardly advanced so that it is proximate the atherectomy site. Again since perfusion is maintained throughout the procedure by perfusion channel 306, dilation can be performed by any of the above methods.

This method finds use for averting occlusive complications. For example, if abrupt closure results from the cutting step, dilation balloon 7 may be immediately advanced for dilation of the occlusion. No time is lost in preparing the balloon or accessing the site. In addition, with atherectomy device 300 perfusion is immediately restored by perfusion channel 306, even during dilation.

The method of the present invention is particularly advantageous for salvaging heart muscle during occlusive complications when compared to prior techniques. Prior atherectomy devices include movable guidewires which may become fixed in the device. Access to the site of the occlusion is lost since the guidewire cannot be left in the vessel when those atherectomy devices are removed; consequently, an angioplasty balloon cannot be placed, or is placed after considerable delay. Even if a guidewire remains, time is lost by introducing a second device.

In contrast, device 300 allows occlusive complications to be treated without delay. Dilation balloon 7 is proximally located from cutter means 57 and may be forwardly advanced for immediate dilation. As a result, heart muscle damage is decreased or eliminated, thereby improving eventual patient outcome. Thus, the advantage of the single device of the present invention is apparent.

The techniques of atherectomy device 300 have several other advantages. Dilation balloon 7 provides uniform opening of the blood vessel which is not available from atherectomy balloon 50 and/or housing 55. As a result, larger luminal areas are achieved with lower restenosis and dissection rates. During simultaneous angioplasty and atherectomy, cutting is enhanced by rearward displacement of stenotic material in response to proximal vessel dilation.

Although only a few embodiments of the present invention have been described, it should be understood that the present invention may be embodied in many other specific forms without departing from the spirit or scope of the invention. Particularly, it should be appreciated that the specific proximal actuator assembly disclosed can be widely varied to affect the required motion for the drive cable and introduction of the necessary fluids. Similarly, the specific construction of the cutting assembly may be varied extensively within the teachings of the present invention while retaining their useful benefit of expanding a channel distally of the dilation balloon. Therefore, the present examples and embodiments are to be considered as illustrative and not restrictive, and the invention is not to be limited to the details given herein, but may be modified within the scope of the appended claims.

What is claimed is:

1. In an atherectomy catheter for removal of at least a portion of a stenosis within a vessel, one elongate flexible tubular member having a torque transmitting layer, at least one lumen extending therethrough, and proximal and distal extremities, the tubular member being adapted for insertion into the vessel, a cutter housing secured to the distal end of the tubular member, flexible drive means disposed within the tubular member for rotational movement within the tubular member, a proximal actuator means for rotating said flexible drive means within the tubular member, and a cutter carried by the distal extremity of the flexible drive means and disposed in the housing for removing at least a portion of the stenosis, an inflatable dilation balloon carried by the tubular member proximally of the cutter housing and having the interior of the balloon in communication with the lumen in the flexible tubular member, means for securing a distal end of the dilation balloon to the exterior surface of the cutter housing, a shrink fit jacket extending over the torque transmitting layer and securing a proximal end of the dilation balloon to the tubular member, means for inflating and deflating the dilation balloon to further reduce the stenosis, and flexible guiding means extending forward of the cutter to travel axially within the vessel.

2. An atherectomy catheter as recited in claim 1 wherein said dilation balloon is mounted coaxially on the tubular member.

3. An atherectomy catheter as recited in claim 2 wherein said dilation balloon circumscribes the tubular member.

4. An atherectomy catheter as recited in claim 1 further comprising:
   collection means for collecting the removed stenosis material.

5. An atherectomy catheter as recited in claim 1 wherein said cutter and flexible drive means are movable axially relative to the tubular member.

6. An atherectomy catheter as recited in claim 5 further comprising a generally cylindrical housing carried by the distal extremity of the tubular member, the housing being formed with a cutout extending longitudinally of the housing on one side of the housing, said cutter being disposed within the housing.

7. An atherectomy catheter as recited in claim 5 further comprising a generally cylindrical housing carried by the distal extremity of the tubular member for receiving the cutter, wherein said cutter has a forwardly extending annular cutting edge, said cutter being movable to an axial position wherein the cutting edge is spaced forwardly from the distal extremity of the housing.

8. An atherectomy catheter as recited in claim 5 wherein said cutter has a plurality of inclined cutting edges arranged to converge towards their distal extremities.

9. An atherectomy catheter as recited in claim 1 wherein the means for securing comprises an exterior recess formed in the housing and a wire carried by the distal extremity of the inflatable balloon for coupling the distal extremity of the balloon to the exterior recess of the housing.

10. A method of reducing stenosis within a vascular vessel to enlarge a fluid flow path within the vessel using an atherectomy catheter comprising one elongate flexible tubular member having a cutter within a housing and a dilation balloon carried proximally of the cutter housing, the method comprising the steps of:
    inserting the catheter into the vessel and advancing the cutter housing to the region of the stenosis using a guidewire which defines a path for the housing;
    cutting a portion of the stenosis from the vessel wall using the cutter in the housing;
    advancing the dilation balloon into the region of the vessel where the stenosis material was removed; and
    expanding the balloon to further expand the flow path where at least some cutting has occurred.

11. A method as recited in claim 10 further comprising the step of collecting the removed stenosis material in a collection chamber formed in a housing formed about the cutter.

12. An atherectomy device for expanding the fluid flow path through a stenosis within a vessel having walls and removing at least a portion of the stenosis, the device including:
    one elongated flexible tubular member having at least one lumen extending therethrough a torque transmitting layer, and shrink fit jacket, the tubular member having proximal and distal extremities and a longitudinal axis;
    flexible drive means disposed within the lumen of the tubular member and adapted for axial and rotational movement therein;
    a proximal actuator assembly for rotating and translating said flexible drive means relative to the longitudinal axis of the tubular member;
    a cutter carried on a distal end of the flexible drive means for removing a portion of the stenosis;
    a cutter housing carried by the distal extremity of the tubular member for receiving the cutter;
    flexible guiding means fixedly attached to the distal end of the cutter housing;
    an inflatable dilation member carried by the tubular member proximally of the housing to expand the fluid flow path; and
    means for inflating and deflating the inflatable dilation member,
    wherein the shrink fit jacket is sized to extend over the proximal end of the inflatable dilation member for securing the inflatable dilation member in place.

13. An atherectomy device comprising:
    a tubular member having a lumen extending between proximal and distal ends thereof;
    a drive member disposed within the lumen of said tubular member;

a dilation balloon disposed at the distal end of said tubular member, said dilation balloon having a first inflation means;

a housing extending from the distal end of said tubular member, said housing having an interior open to the lumen of the drive member, an aperture on one side thereof, and having an atherectomy balloon on an opposite side thereof, said atherectomy balloon having a second inflation means;

a cutter disposed within said housing and coupled to said drive member; and means for maintaining blood flow past said dilation balloon, said means comprising at least one perfusion hole positioned on the tubular means proximal to the dilation balloon for permitting blood flow into the lumen of the tubular member, whereby said blood flow can pass out through the aperture of the housing.

14. A method for treating atherosclerosis in a blood vessel, said method comprising:

positioning a device within the blood vessel proximate stenotic material, said device having a cutting means disposed at a distal end thereof and having a dilation balloon disposed proximal to said cutting means, said device further including means for maintaining blood flow past said dilation balloon;

severing the stenotic material with said cutting means, whereby the vessel is subject to abrupt reclosure; and dilating the stenotic material with said dilation balloon, substantially immediately after the severing step, wherein blood flow is maintained past the dilation balloon by the means for maintaining blood flow.

15. The method of claim 14, wherein said dilating step comprises inflating the dilation balloon so that the stenotic material is predominantly severed at the beginning of the method and predominantly dilated at the end of the method.

16. The method of claim 14, wherein said dilating step comprises:

inflating the dilation balloon; and thereafter deflating the dilation balloon so that the stenotic material is predominantly dilated at the beginning of the method and predominantly severed at the end of the method.

17. A method for treating atherosclerosis in a blood vessel, said method comprising:

positioning a device within the blood vessel proximate a stenosis, said device having a housing with an elongate side aperture secured to a distal end thereof, a cutting means disposed within the housing, and a dilation balloon disposed proximal to said housing, said device further including means for maintaining blood flow past said dilation balloon, and into the housing;

severing the stenosis with said cutting means; thereafter immediately advancing said device for positioning said dilation balloon proximate said stenosis; and inflating said dilation balloon to dilate the stenosis while the cutting means is positioned relative to the housing to permit blood flow out through the side aperture of the housing.

18. A method for reducing stenosis in a blood vessel and treating abrupt closure of the blood vessel, said method comprising:

positioning a device within the blood vessel proximate a stenosis, said device having a housing with an elongate side aperture secured to a distal end thereof, a cutting means disposed within the housing, and a dilation balloon disposed proximal to said housing, said device further including means for maintaining blood flow past said dilation balloon and into the housing;

severing the stenosis with said cutting means;

if the blood vessel abruptly closes, immediately advancing said device for positioning said dilation balloon proximate said stenosis; and inflating said dilation balloon to dilate the stenosis while the cutting means is positioned relative to the housing to permit blood flow out through the side aperture of the housing.

19. A method for treating atherosclerosis in a blood vessel, said method comprising:

positioning a device within the blood vessel proximate a stenosis, said device having a housing with an elongate side aperture secured to a distal end thereof, a cutting means disposed within the housing, and a dilation balloon disposed proximal to said housing, said device further including means for maintaining blood flow past said dilation balloon and into the housing;

dilating the stenosis with said dilation balloon; thereafter immediately retracting said device for positioning said cutting means proximate said stenosis; and severing the stenosis with said cutting means.

* * * * *